(12) United States Patent
Yamaguchi et al.

(10) Patent No.: US 9,095,560 B2
(45) Date of Patent: Aug. 4, 2015

(54) METHOD OF ENHANCING TRANSDERMAL ABSORPTION USING A COMPOSITION COMPRISING POE OCTYL DODECYL ETHER AND SQUALANE

(75) Inventors: Yoko Yamaguchi, Kanagawa (JP); Rie Igarashi, Kanagawa (JP)

(73) Assignees: JAPAN SCIENCE AND TECHNOLOGY AGENCY, Tsukuba-shi (JP); NANOEGG RESEARCH LABORATORIES, INC., Kawasaki-shi (JP)

(*) Notice: Subject to any disclaimer, the term of this patent is extended or adjusted under 35 U.S.C. 154(b) by 202 days.

(21) Appl. No.: 12/876,616

(22) Filed: Sep. 7, 2010

(65) Prior Publication Data
US 2011/0081418 A1    Apr. 7, 2011

Related U.S. Application Data

(63) Continuation of application No. 11/912,964, filed as application No. PCT/JP2006/308975 on Apr. 28, 2006, now abandoned.

(30) Foreign Application Priority Data

Apr. 28, 2005  (JP) ................. 2005-130962

(51) Int. Cl.
| A61P 3/10 | (2006.01) |
|---|---|
| A61P 17/02 | (2006.01) |
| A61K 9/06 | (2006.01) |
| A61K 31/23 | (2006.01) |
| A61K 9/00 | (2006.01) |
| A61K 9/127 | (2006.01) |
| A61K 31/203 | (2006.01) |
| A61K 47/12 | (2006.01) |
| A61K 47/44 | (2006.01) |

(52) U.S. Cl.
CPC ............ *A61K 31/23* (2013.01); *A61K 9/0014* (2013.01); *A61K 9/06* (2013.01); *A61K 9/1274* (2013.01); *A61K 31/203* (2013.01); *A61K 47/12* (2013.01); *A61K 47/44* (2013.01)

(58) Field of Classification Search
None
See application file for complete search history.

(56) References Cited

U.S. PATENT DOCUMENTS

| 4,940,576 | A |   | 7/1990 | Walsh |  |
|---|---|---|---|---|---|
| 5,456,915 | A |   | 10/1995 | Nagase et al. |  |
| 5,500,416 | A | * | 3/1996 | Miyazawa et al. | 514/23 |
| 5,688,493 | A |   | 11/1997 | Sugawara et al. |  |
| 5,688,831 | A |   | 11/1997 | El-Nokaly et al. |  |
| 5,696,074 | A |   | 12/1997 | Nickel et al. |  |
| 5,871,760 | A |   | 2/1999 | Doughty et al. |  |
| 6,224,888 | B1 |   | 5/2001 | Vatter et al. |  |
| 6,238,653 | B1 |   | 5/2001 | Narasimhan et al. |  |
| 6,488,945 | B2 |   | 12/2002 | Sato |  |
| 6,709,664 | B2 | * | 3/2004 | Resnick | 424/401 |
| 2004/0028643 | A1 |   | 2/2004 | Chiba et al. |  |
| 2004/0185113 | A1 | * | 9/2004 | Mizushima et al. | 424/490 |
| 2004/0202705 | A1 | * | 10/2004 | Xiong et al. | 424/449 |
| 2007/0014863 | A1 |   | 1/2007 | Yamaguchi et al. |  |
| 2007/0243144 | A1 |   | 10/2007 | Takagaki |  |

FOREIGN PATENT DOCUMENTS

| DE | 4238779 A1 | 5/1994 |  |  |
|---|---|---|---|---|
| JP | 62-096585 A | 5/1984 |  |  |
| JP | 63-126544 A | 5/1988 |  |  |
| JP | 1-53845 B2 | 11/1989 |  |  |
| JP | 02-078432 A | 3/1990 |  |  |
| JP | 03-074313 A | 3/1991 |  |  |
| JP | 08-099856 A | 4/1996 |  |  |
| JP | 11-139924 A | 5/1999 |  |  |
| JP | 11-506125 A | 6/1999 |  |  |
| JP | 2001-524958 A | 12/2001 |  |  |
| JP | 2002-053436 A | 2/2002 |  |  |
| JP | 2004-161739 A | 6/2004 |  |  |
| KR | 2001011004 A | 2/2001 |  |  |
| KR | 2001098134 A | 11/2001 |  |  |
| WO | 94/28860 A1 | 12/1994 |  |  |
| WO | 02/096396 A1 | 12/2002 |  |  |
| WO | 03-106168 A1 | 12/2003 |  |  |
| WO | WO 2005/032514 | * | 4/2005 | ............. A61K 9/06 |
| WO | 2005-070413 A1 | 8/2005 |  |  |

OTHER PUBLICATIONS

Makai et al. Surfactant properties of nonionic surfactant/glycerol/paraffin lyotropic liquid crystals, Colloid Polym Sci. (2003) 281: 839-844.*

Memişoğlu, E., et al. Pharm. Dev. Tech. (1997), 2(2); pp. 171-180.*

Muller-Goymann, "Physicochemical characterization of colloidal drug delivery systems such as reverse micelles, vesicles, liquid crystals and nanoparticles for topical administration", European Journal of Pharmaceutics and Biopharmaceutics, Elsevier Science Publishers B.V.., Amsterdam, NL, vol. 58, No. 2, Sep. 1, 2004, pp. 343-356, XP004526317.

European Office Action dated Jan. 5, 2012, issued in corresponding European Patent Application No. 06745834.9.

Nikko Chemicals Co., Ltd., "Cosmetics Handbook", dated Nov. 11, 1996, pp. 455-457.

(Continued)

*Primary Examiner* — Kevin S Orwig
(74) *Attorney, Agent, or Firm* — Westerman, Hattori, Daniels & Adrian, LLP

(57) ABSTRACT

An object of the present invention is to provide a transdermal absorption enhancer by which various active ingredients are transdermally absorbed. In accordance with a transdermal absorption enhancer of the present invention which effective ingredient is lyotropic liquid crystal which has been utilized as a basic material for pharmaceutical preparations for external application and for cosmetics, transdermal absorption of a macromolecular substance and a water-soluble substance was able to be improved.

11 Claims, 7 Drawing Sheets

(56) References Cited

OTHER PUBLICATIONS

European Search Report dated Jul. 28, 2009, issued in corresponding European Patent Application No. 06745834.

Yamaguchi Y. et al. "Successful treatment of photo-damaged skin of nano-scale atra particles using a novel transdermal delivery" Journal of Controlled Release, Elsevier. Amsterdam, NL, vol. 104, No. 1, May 5, 2005, pp. 29-40, XP004872698.

Yamaguchi et al., JP 2004-161739 machine translation, Jun. 10, 2004.

D. I. Nesseem et al.; "Formulation and evaluation of itraconazole via liquid crystal for topical delivery system", J. Pharm. Biomed. Anal., 2001, pp. 387-399, vol. 26.

International Search Report of PCT/JP2006/308975, date of mailing Jul. 18, 2006.

I. Csoka et al; "In vitro and in vivo percutaneous absorption of topical dosage forms: case studies", Int. J. Pharm., Mar. 3, 2005, pp. 11-19, vol. 291, No. 1-2.

D.W. Osborne et al.; "Lyotropic Liquid Crystals as Topical Drug Delivery Vehicles", Ind. J. Pharm. Adv., 1995, pp. 38-45, vol. 1, No. 1.

N. H. Gabboun et al.; "Release of salicylic acid, diclofenac acid and diclofenac acid salts form isotrropic and anisotropic nonionic surfactant system across rat skin", Int. J. Pharm., 2001, pp. 73-80, vol. 212.

M. Makai et al.; "Structural properties of nonionic surfactant/ glycero/paraddin lyotropic liquid crystals", Colloip Polym. Sci., 2003, pp. 839-844, vol. 281.

Toshiyuki Suzuki "Ekisho de Keshohin o Tsukuru", Chemistry & Chemical Industry, 1998, pp. 1208-1211, vol. 51, No. 8.

Notification of Reason for Refusal issued on Oct. 23, 2009 in corresponding Chinese Patent Application No. 200680019033.4.

Encyclopedia of Cosmetic Chemistry and Technology, pp. 959-960, 1997.

* cited by examiner

In each of the above, the data after 1 day, 2 days and 3 days are shown from left to right In each of the above, the data after 1 day, 2 days and 3 days are shown from left to right Control (water)　　　Water/α-arbutin　　　Water/β-arbutin Liquid crystal only　　Liquid crystal/α-arbutin　　Liquid crystal/β-arbutin

FITC-Dextran 70K

METHOD OF ENHANCING TRANSDERMAL ABSORPTION USING A COMPOSITION COMPRISING POE OCTYL DODECYL ETHER AND SQUALANE

CROSS-REFERENCE TO RELATED APPLICATIONS

This application is a divisional application of U.S. application Ser. No. 11/912,964, filed Oct. 29, 2007, which is a National Phase Application of PCT/JP2006/308975, filed Apr. 28, 2006, which is based upon and claims the benefit of priority from Japanese Patent Application No. 2005-130962, filed Apr. 28, 2005, the entire contents of all of which are incorporated herein by reference.

TECHNICAL FIELD

The present invention relates to a transdermal absorption enhancer by which various active ingredients are transdermally absorbed.

BACKGROUND ART

Transdermal administration is easy and convenient as compared with oral administration and administration by injection, and may also be advantageous in terms of duration of the effect and reduction of expression of the side effects, whereby that is an excellent administration method. However, in order to permeate the active ingredient into the body by transdermal administration, the active ingredient is to be penetrated through the skin which constitutes the primary barrier of the living body and, therefore, its bioavailability (amount of the drug absorbed with a blood flow) is inherently low. Accordingly, in order to achieve the improvement of bioavailability of active ingredients, it has been conducted that dipropylene glycol, hexylene glycol, isoparaffin, sodium laurylsulfate, an ethylene oxide adduct of lauryl alcohol, polyethylene glycol fatty acid ester, polyoxyethylene sorbitan fatty acid ester, propyl carbonate, sodium pyrrolidonecarboxylate, urea, lactic acid, sodium lactate, lecithin, dimethyl sulfoxide, pyrrolidonecarboxylate, nicotinate, N-methylproline ester, cholesteryl oleate, amine oxide or the like is compounded with preparations for external application as a transdermal absorption enhancer.

Up to now, the present inventors have energetically carried out research and development for transdermal absorption of active ingredients and, as a result, they have found that, when retinoic acid having an action of enhancing regeneration of the skin by enhancing differentiation and growth of keratinocytes is included into capsules of a nanometer level (nano-particles) followed by applying to the skin surface, retinoic acid is able to be transdermally absorbed in efficient and sustained-releasing manner without compounding of the transdermal absorption enhancers as mentioned above (Non-Patent Document 1 and Non-Patent Document 2).

Non-Patent Document 1: Yoko Yamaguchi, "Novel Nano-Technology for Transdermal Delivery", Bio Venture, vol. 4, no. 6, pages 62 to 64, 2004

Non-Patent Document 2: Y. Yamaguchi, T. Nagasawa, N. Nakamura, M. Takenaga, M. Mizoguchi, S. Kawai, Y. Mizushima and R. Igarashi, "Successful Treatment of Photo-Damaged Skin of Nano-Scale atRA Particles Using a Novel Transdermal Delivery", 104, 29 to 40, 2005.

DISCLOSURE OF THE INVENTION

Problems that the Invention is to Solve

Although the above-mentioned nano-particle including retinoic acid therein is expected for its clinical application as a method for transdermal absorption of retinoic acid with little irritation of retinoic acid to the skin, investigation of methods for transdermal absorption of various active ingredients is still meaningful.

Accordingly, an object of the present invention is to provide a transdermal absorption enhancer by which various active ingredients are transdermally absorbed.

Means for Solving the Problems

In view of the above, the present inventors have repeatedly conducted intensive investigations and, as a result, they have found that lyotropic liquid crystal (refer, for example, to Japanese Patent Nos. 2,547,151 and 3,459,253) which has been already known as a basic material for pharmaceutical preparations for external application and for cosmetics has an action of enhancing the transdermal absorption of various active ingredients.

The transdermal absorption enhancer of the present invention achieved on the basis of the above finding is characterized in that lyotropic liquid crystal is an effective ingredient as mentioned in claim 1.

The transdermal absorption enhancer mentioned in claim 2 is characterized in that, in the transdermal absorption enhancer according to claim 1, the lyotropic liquid crystal contains 5% by weight to 80% by weight of a surfactant and 5% by weight to 80% by weight of water.

The transdermal absorption enhancer mentioned in claim 3 is characterized in that, in the transdermal absorption enhancer according to claim 2, the surfactant is a nonionic surfactant and/or lecithin.

The transdermal absorption enhancer mentioned in claim 4 is characterized in that, in the transdermal absorption enhancer according to claim 3, the nonionic surfactant is at least one member selected from the group consisting of polyoxyethylene alkyl ether, polyoxyethylene sorbitan fatty acid ester and polyoxyethylene hydrogenated castor oil.

The transdermal absorption enhancer mentioned in claim 5 is characterized in that, in the transdermal absorption enhancer according to claim 2, the lyotropic liquid crystal further contains 1% by weight to 80% by weight of oil.

The transdermal absorption enhancer mentioned in claim 6 is characterized in that, in the transdermal absorption enhancer according to claim 5, the oil is squalane.

The transdermal absorption enhancer mentioned in claim 7 is characterized in that, in the transdermal absorption enhancer according to claim 2, the lyotropic liquid crystal further contains 1% by weight to 55% by weight of a polyhydric alcohol.

The transdermal absorption enhancer mentioned in claim 8 is characterized in that, in the transdermal absorption enhancer according to claim 7, the polyhydric alcohol is glycerol.

The transdermal absorption enhancer mentioned in claim 9 is characterized in that, in the transdermal absorption enhancer according to claim 2, the lyotropic liquid crystal further contains 0.01% by weight to 10% by weight of an auxiliary surfactant.

The transdermal absorption enhancer mentioned in claim 10 is characterized in that, in the transdermal absorption enhancer according to claim 9, the auxiliary surfactant is cholesterol.

In addition, a transdermal absorption composition of the present invention is characterized in that, lyotropic liquid crystal is compounded with an active ingredient as mentioned in claim 11.

The transdermal absorption composition mentioned in claim 12 is characterized in that, in the transdermal absorption composition according to claim 11, the active ingredient is at least one member selected from the group consisting of organic compound, peptide, protein, oligonucleotide, DNA and RNA.

The transdermal absorption composition mentioned in claim 13 is characterized in that, in the transdermal absorption composition according to claim 11, the active ingredient is a macromolecular substance where molecular weight is not less than 1,000 or a water-soluble substance.

The transdermal absorption composition mentioned in claim 14 is characterized in that, in the transdermal absorption composition according to claim 11, the active ingredient is compounded in a form of being included in the inside of fine particles of inorganic acid salt with divalent metal.

The transdermal absorption composition mentioned in claim 15 is characterized in that, in the transdermal absorption composition according to claim 11, the active ingredient is compounded in an amount of 0.01% by weight to 50% by weight to the lyotropic liquid crystal.

Advantages of the Invention

In accordance with the present invention, there is provided a transdermal absorption enhancer as a novel pharmaceutical use of lyotropic liquid crystal which has been utilized as a basic material for pharmaceutical preparations for external application and for cosmetics and, in the transdermal absorption enhancer of the present invention, various active ingredients are able to be transdermally absorbed.

BEST MODE FOR CARRYING OUT THE INVENTION

Figure 1:
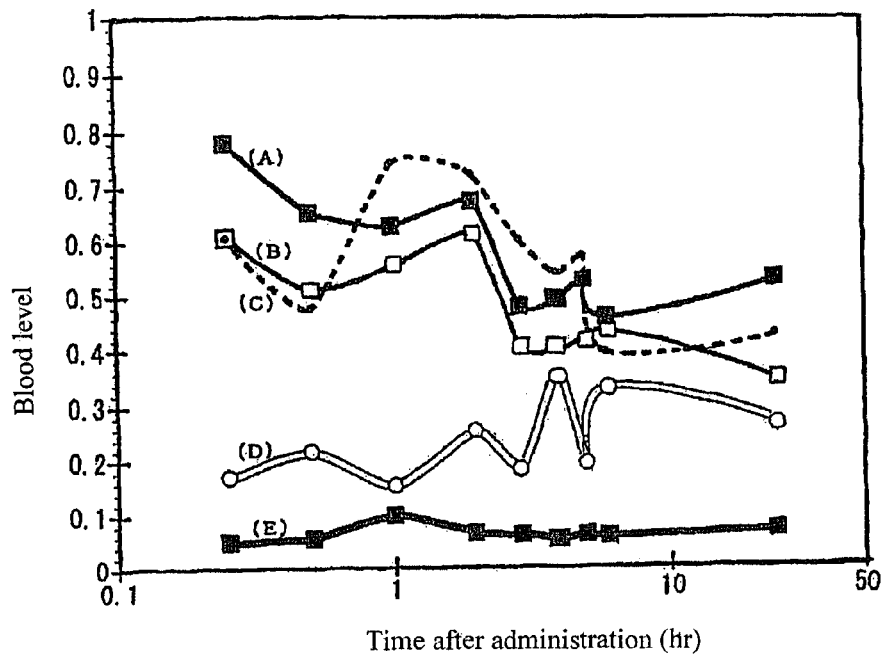
FIG. 1 is a graph which shows the changes in concentration of retinoic acid in blood in Example 1.

The transdermal absorption enhancer of the present invention is characterized in that lyotropic liquid crystal is an effective ingredient. The lyotropic liquid crystal in accordance with the present invention means such a thing that, in a system where surfactant (amphipathic molecule having a hydrophilic part and a hydrophobic (lipophilic) part in a molecule) and water are coexisting, a liquid crystal state (a state where a predetermined regularity in molecular orientation is maintained as if in the case of crystal while fluidity is still available as if in the case of liquid) is formed depending upon the mixing ratio of both parts and upon temperature. Principally, it is able to be understood that, in lyotropic liquid crystal, when water is added, within a predetermined temperature range, to a surfactant in a solid state having a crystal structure where hydrophobic parts (hydrophobic groups such as alkyl group) are faced each other, said parts lose regularity due to thermal movement resulting in a liquid state and then the hydrophilic parts act each other due to hydrogen bond to maintain for a long period whereby an associated structure (such as hexagonal structure and lamella structure) is resulted (refer, if necessary, to Toshiyuki Suzuki, "Liquid Crystal", vol. 2, pages 194 to 201, 1998).

With regard to the surfactant which is a constituting component of the lyotropic liquid crystal, there is no particular limitation so far as it is able to form a liquid crystal state (a periodical structure where the interplanar spacing is 10 nm to 800 nm is particularly preferred) in a system coexisting with water depending upon the mixing ratio with water and upon temperature. Thus, it may be a surfactant of any of the types of nonionic type, anionic type, cationic type and amphoteric type and may also be a surfactant derived from nature such as lecithin (for example, egg yolk lecithin and soybean lecithin) and saponin. A single surfactant may be used solely or plural kinds thereof may be mixed and used.

Examples of the nonionic surfactant are polyoxyethylene alkyl ether, polyoxyethylene alkyl phenol ether, alkyl glucoside, polyoxyethylene fatty acid ester, sucrose fatty acid ester, sorbitan fatty acid ester, polyoxyethylene sorbitan fatty acid ester, fatty acid alkanolamide and polyoxyethylene hydrogenated castor oil. Examples of the anionic surfactant are soap (sodium salt, potassium salt, etc. of fatty acid), alkylbenzenesulfonate (such as sodium salt), higher alcohol sulfate salt (such as sodium salt), polyoxyethylene alkyl ether sulfate (such as sodium salt), $\alpha$-sulfofatty acid ester, $\alpha$-olefin sulfonate (such as sodium salt), monoalkylphosphate salt (such as sodium salt) and alkanesulfonate (such as sodium salt). Examples of the cationic surfactant are alkyl trimethylammonium salt (such as chloride), dialkyl dimethylammonium salt (such as chloride), alkyl dimethylbenzylammonium salt (such as chloride) and amine salt (such as acetate salt and hydrochloride salt). Examples of the amphoteric surfactant are alkylamino fatty acid salt (such as sodium salt), alkylbetaine and alkylamine oxide. Rate of the surfactant in the lyotropic liquid crystal is preferably 5% by weight to 80% by weight, more preferably 7% by weight to 70% by weight and, still more preferably, 10% by weight to 65% by weight. HLB value of the surfactant is preferably not less than 8, more preferably not less than 10 and, still more preferably, not less than 12.

With regard to water which is a constituting component of the lyotropic liquid crystal, distilled water or the like may be used. Water used therefor may contain organic solvent which is miscible with water such as ethanol and isopropanol. Rate of water in the lyotropic liquid crystal is preferably 5% by weight to 80% by weight, more preferably 10% by weight to 60% by weight and, still more preferably, 13% by weight to 50% by weight.

The lyotropic liquid crystal may further contain oil besides the surfactant and water. When oil is contained therein, the liquid crystal structure becomes similar to a lamella structure formed by the intercellular lipid in a horny layer and, upon application to the skin surface, a phase transfer of the intercellular lipid structure is apt to happen and, as a result, an excellent enhancing action of transdermal absorption is achieved for the active ingredient. Examples of the oil are vegetable oil such as wheat germ oil, corn oil, sunflower oil and castor oil; silicone oil; ester oil such as isopropyl myristate, glyceryl trioctanoate, diethylene glycol monopropylene pentaerythritol ether and pentaerythrityl tetraoctanoate; squalane; squalene; liquid paraffin; and polybutene. A single oil may be used solely or plural kinds thereof may be mixed and used. Rate of the oil in the lyotropic liquid crystal is preferably 1% by weight to 80% by weight, more preferably 5% by weight to 70% by weight and, still more preferably, 10% by weight to 65% by weight.

The lyotropic liquid crystal may further contain a polyhydric alcohol. When a polyhydric alcohol is contained therein, it is possible to attempt for making the formation of liquid crystal structure easy (expansion of phase region) and for making it stable. Examples of the polyhydric alcohol are polyalkylene glycol (such as polyethylene glycol and polyalkylene glycol), glycerol, propylene glycol, 1,3-propanediol, 2-butene-1,4-diol, pentane-1,5-diol, 2,2-dimethylpropane-1,3-diol, 3-methylpentane-1,5-diol, pentane-1,2-diol, 2,2,4-trimethylpentane-1,3-diol, 2-methylpropane-1,3-diol, hexylene glycol, 1,3-butylene glycol, dipropylene glycol, diethylene glycol and triethylene glycol. A single polyhydric alcohol may be used solely or plural kinds thereof may be mixed and used. Rate of the polyhydric alcohol in the lyotropic liquid crystal is preferably 1% by weight to 55% by weight, more preferably 3% by weight to 52% by weight and, still more preferably, 5% by weight to 50% by weight.

The lyotropic liquid crystal may further contain an auxiliary surfactant such as cholesterol. When an auxiliary surfactant is contained therein, reduction of surface membrane curvature is able to be achieved even when various kinds of surfactants are used and, therefore, it is able to attempt for making the formation of liquid crystal structure easy and for making it stable. Rate of the auxiliary surfactant in the lyotropic liquid crystal is preferably 0.01% by weight to 10% by weight.

The lyotropic liquid crystal is able to be prepared by mixing of the surfactant and water which are constituting components thereof in a predetermined ratio at predetermined temperature. If necessary, an operation where the constituting component is temporarily warmed before or after mixing may be carried out.

In the transdermal absorption enhancer of the present invention, various active ingredients are able to be transdermally absorbed independently of physical and chemical properties thereof. Here, "active ingredient" means that which is able to act as a drug for attempting prevention and treatment of various diseases and maintenance and improvement of health and beauty for mammals including human being and, to be more specific, its examples are vitamins, prostaglandins, anti-cancer drug, growth hormones, various growth factors, vaccine antigen, gene encoding useful protein and other organic compound, peptide, protein, oligonucleotide, DNA and RNA. The matter being worthy of special mention for the transdermal absorption enhancer of the present invention is that transdermal absorption of substances which have been impossible or difficult to be penetrated into the skin and permeated into the body such as macromolecular substances where molecular weight is 1,000 or more (although there is no particular limitation for the upper limit of the molecular weight, it is, for example, 500,000 to 1,000,000) and water-soluble substances such as niacinamide (nicotinamide) (the water-soluble substance may be defined, for example, as "a substance which shows a transmittance (1/absorbance) of within a range of 70% to 100% at 450 nm wavelength in a state of being dispersed in water and, when its appearance is observed, no macroscopic separation is noted") is now made possible.

Since lyotropic liquid crystal which has been utilized as a basic material for pharmaceutical preparations for external application and for cosmetics is an effective ingredient of the transdermal absorption enhancer of the present invention, it is now possible to prepare a transdermally absorption composition when the lyotropic liquid crystal is compounded with an active ingredient. Compounding amount of the active ingredient to the lyotropic liquid crystal is, for example, from 0.01% by weight to 50% by weight. When the lyotropic liquid crystal is compounded, for example, with a substance having an enhancing action of differentiation and growth of keratinocytes, a substance having a suppressive action to melanin pigment production or a substance having an enhancing action for the synthesis of intercellular lipid of horny layer, it is now possible to prepare a dermal regeneration enhancing composition where aging of the skin, generation of spots, etc. are effectively able to be suppressed. Examples of the substances having an enhancing action of differentiation and growth of keratinocytes are retinal, 3-dehydroretinal, retinoic acid, 3-dehydroretinoic acid, substances similar to retinoic acid, retinol, retinol fatty acid ester and 3-dehydroretinol fatty acid ester. Examples of the substances having a suppressive action to melanin pigment production are ascorbic acid glucoside, arbutin and superoxide dismutase (SOD). Examples of the substances having an enhancing action for the synthesis of intercellular lipid of horny layer are niacinamide, etc. Such a substance itself may be uniformly dispersed in the lyotropic liquid crystal followed by being incorporated among the phases of the liquid crystal structure so that it is compounded, or it may be included in the inside of fine particles of inorganic acid salt with divalent metal such as fine particles where diameter is 100 nm to 1,000 nm comprising calcium carbonate, magnesium carbonate, zinc carbonate, calcium phosphate, magnesium phosphate and zinc phosphate (with regard to a method therefor, refer, if necessary, to WO 02/096396) and the fine particles (nano-particles) into which such a substance is included are uniformly dispersed in the lyotropic liquid crystal followed by being incorporated among the phases of the liquid crystal structure so that they are compounded. In addition, a divalent metal ion and a counterion thereof are adsorbed on the surface (surface membrane) of the lyotropic liquid crystal so as to enhance the viscoelasticity of the membrane, whereby the physical and chemical stability of the substance incorporated among the phases is able to be improved. It is further possible to utilize in such a manner that the transdermal absorption enhancer of the present invention is previously applied on the skin surface and then the active ingredient is added thereto whereby transdermal absorption is conducted.

The transdermal absorption enhancer of the present invention may be directly applied to the skin surface as a preparation for external application or may be applied to the skin surface after dispersing in an ointment base, a cream base or a lotion base. It goes without saying that, in making into the preparations, known components such as antiseptic, moisturizer or antioxidant is appropriately added thereto.

EXAMPLES

Example 1

Step 1

Nano-particles comprising the three kinds of formulations as mentioned in Table 1 in which retinoic acid (an all-trans substance; hereinafter, it has the same meaning) as an active ingredient was included were prepared as follows.

Retinoic acid, ethanol and a 1N aqueous solution of sodium hydroxide were placed in a beaker so that retinoic acid was uniformly dissolved. Then, glycerol and Emulgen 2020G-HA (polyoxyethylene octyl dodecyl ether) which is a trade name of a nonionic surfactant manufactured by Kao were added thereto followed by stirring for about 10 minutes. Then distilled water was added thereto and the mixture was stirred for about 10 minutes to give a mixed micelle of retinoic acid and the nonionic surfactant. After that, a 5M aqueous solution of magnesium chloride or a 5M aqueous solution of calcium chloride was added thereto followed by stirring for about 1 hour. Finally, a 1M aqueous solution of sodium carbonate was added thereto and the mixture was stirred for about 1 hour to give nano-particles in which retinoic acid was included in a thin film of magnesium carbonate or in a thin film of calcium carbonate where the diameter was 10 nm to 1,000 nm.

TABLE 1

|  | Formulation 1 | Formulation 2 | Formulation 3 |
|---|---|---|---|
| Retinoic Acid | 140 mg | 280 mg | 560 mg |
| Ethanol | 400 µL | 800 µL | 1600 µL |
| 1N Aqueous Solution of Sodium Hydroxide | 560 µL | 1120 µL | 2240 µL |
| Glycerol | 5 mL | 5 mL | 5 mL |
| Distilled Water | 17.72 mL | 16.76 mL | 14.28 mL |
| Nonionic Surfactant | 2 mL | 2 mL | 2 mL |
| 5M Aqueous Solution of $MgCl_2$ or $CaCl_2$ | 46.5 µL | 93 µL | 186 µL |
| 1M Aqueous Solution of Sodium Carbonate | 46.5 µL | 93 µL | 186 µL |

Step 2

31 mL of glycerol was added to a beaker in which 17 mL of distilled water was placed so that it was uniformly dissolved. Then 28 mL of Emulgen 2020G-HA was added thereto and uniformly dispersed therein. Since viscosity of the solution increased at that time, such a phenomenon was used as a yardstick for the uniform dispersion of each of the materials. After that, 20 mL of squalane was added to uniformly mix therewith, then 10 mL of squalane was further added and the mixture was stirred for about 5 minutes. More 5 mL of squalane was added and the mixture was stirred, whereupon viscosity of the solution gradually rose and it was instantly gelled. This phenomenon was used as a yardstick for the formation of the liquid crystal. After that, stirring was still continued for several minutes to give lyotropic liquid crystal (comprising 28.0% by weight of surfactant, 16.0% by weight of water, 25.0% by weight of oil and 31.0% by weight of polyhydric alcohol). The nano-particles prepared in the step 1 were compounded with the lyotropic liquid crystal so as to make the compounding amount of retinoic acid 0.1% by weight (formulation 1), 0.2% by weight (formulation 2) or 0.4% by weight (formulation 3) to the lyotropic liquid crystal to give the lyotropic liquid crystal where the nano-particles in which retinoic acid was included were uniformly dispersed without degradation. Incidentally, all of the above operations were carried out under shielding the light and the nonionic surfactant was used after being melted at about 60° C. (hereinafter, that is also the same).

Back of Wistar rats (seven weeks age; male) was shaved, the shaved part was washed with lukewarm water, each 30 mg of the lyotropic liquid crystals compounded with nano-particles in which the retinoic acid was included according to the above formulation 1 (liquid crystal compounded with fine particles of magnesium carbonate in which retinoic acid was included and liquid crystal compounded with fine particles of calcium carbonate in which retinoic acid was included) was applied to an area of 2 cm×5 cm thereof and concentration of retinoic acid in blood was measured. As a comparative example, retinoic acid in the same dose was hypodermically injected and concentration of retinoic acid in blood was measured. Further, instead of the lyotropic liquid crystal compounded with the nano-particles in which retinoic acid was included, each of vaseline compounded with nano-particles in which retinoic acid was included (fine particles of calcium carbonate in which retinoic acid was included) so as to make the compounding amount of retinoic acid same as that of the liquid crystal of the formulation 1 and vaseline compounded with retinoic acid itself so as to make the compounding amount retinoic acid same as that of the liquid crystal of the formulation 1 was applied and concentration of retinoic acid in blood was measured. The result is shown in FIG. 1. Incidentally, (A) to (E) in FIG. 1 are as follows.

(A): The result where the lyotropic liquid crystal compounded with fine particles of magnesium carbonate in which retinoic acid was included was applied (B): The result where the lyotropic liquid crystal compounded with fine particles of calcium carbonate in which retinoic acid was included was applied (C): The result where retinoic acid was hypodermically injected (D): The result where vaseline compounded with fine particles of calcium carbonate in which retinoic acid was included was applied (E): The result where vaseline compounded with retinoic acid itself was applied As will be apparent from FIG. 1, concentrations of retinoic acid in blood when the lyotropic liquid crystal compounded with fine particles of magnesium carbonate in which retinoic acid was included was applied and when the lyotropic liquid crystal compounded with fine particles of calcium carbonate in which retinoic acid was included was applied were nearly the same as the concentration of retinoic acid in blood when retinoic acid was hypodermically injected, whereupon it was found that the lyotropic liquid crystal had an enhancing action of transdermal absorption.

Example 2

Figure 2:
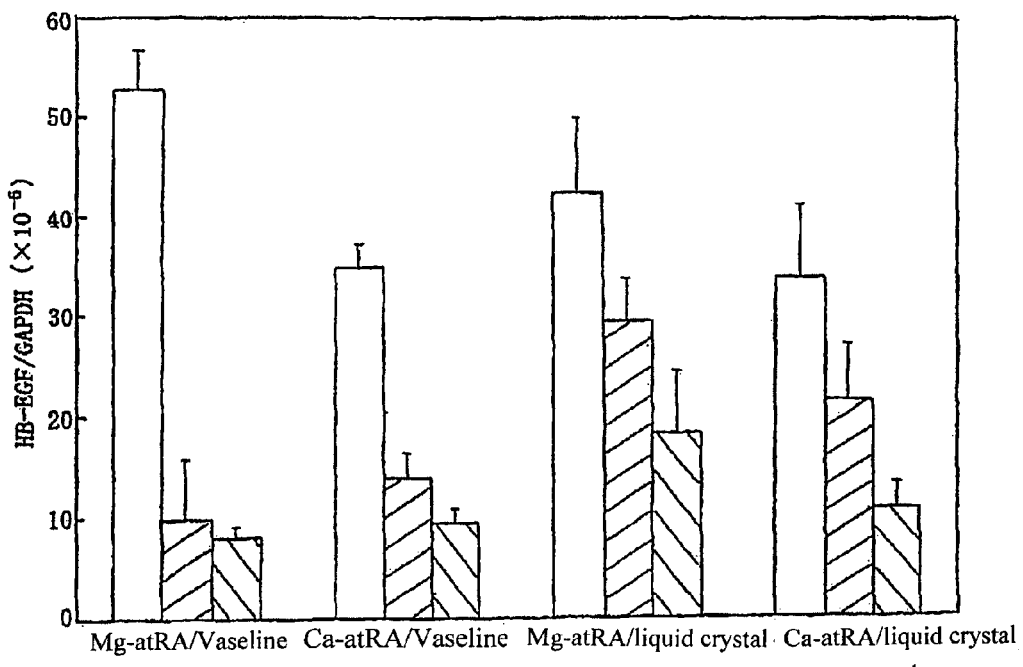
FIG. 2 is a graph which shows the changes in production amount of HB-EGF when each of the four kinds of samples is applied in Example 2.

Back of ddY mice (seven weeks age; male) was shaved, the shaved part was washed with lukewarm water and each 30 mg of the following four kinds of samples was applied to an area of 1.5 cm×1.5 cm thereof. Changes in the production amount of HB-EGF (heparin-binding EGF-like growth factor) playing a role of dermal regeneration function after 1 day, 2 days and 3 days from the application date were measured (refer, if necessary, to Non-Patent Document 2 for the details of the measuring means), whereby each effects to transdermal absorption of retinoic acid was evaluated. The result is shown in FIG. 2. As will be apparent from FIG. 2, when fine particles of magnesium carbonate in which retinoic acid was included was compounded with the lyotropic liquid crystal and when fine particles of calcium carbonate in which retinoic acid was included were compounded with the lyotropic liquid crystal, the production amounts of HB-EGF after 2 days and 3 days from the application date were much more as compared with the case where they were compounded with vaseline, whereby it was found that transdermal absorption of retinoic acid was improved by the enhancing action of transdermal absorption of the lyotropic liquid crystal.

(a) Lyotropic liquid crystal compounded with fine particles of magnesium carbonate in which retinoic acid was included according to the formulation 1 of Example 1 (Mg-atRA/liquid crystal)

(b) Lyotropic liquid crystal compounded with fine particles of calcium carbonate in which retinoic acid was included according to the formulation 1 of Example 1 (Ca-atRA/liquid crystal)

(c) Vaseline compounded with fine particles of magnesium carbonate in which retinoic acid was included so as to make the compounding amount of retinoic acid same as that of the liquid crystal of the formulation 1 of Example 1 (Mg-atRA/vaseline)

(d) Vaseline compounded with fine particles of calcium carbonate in which retinoic acid was included so as to make the compounding amount of retinoic acid same as that of the liquid crystal of the formulation 1 of Example 1 (Ca-atRA/vaseline)

Example 3

Figure 3:
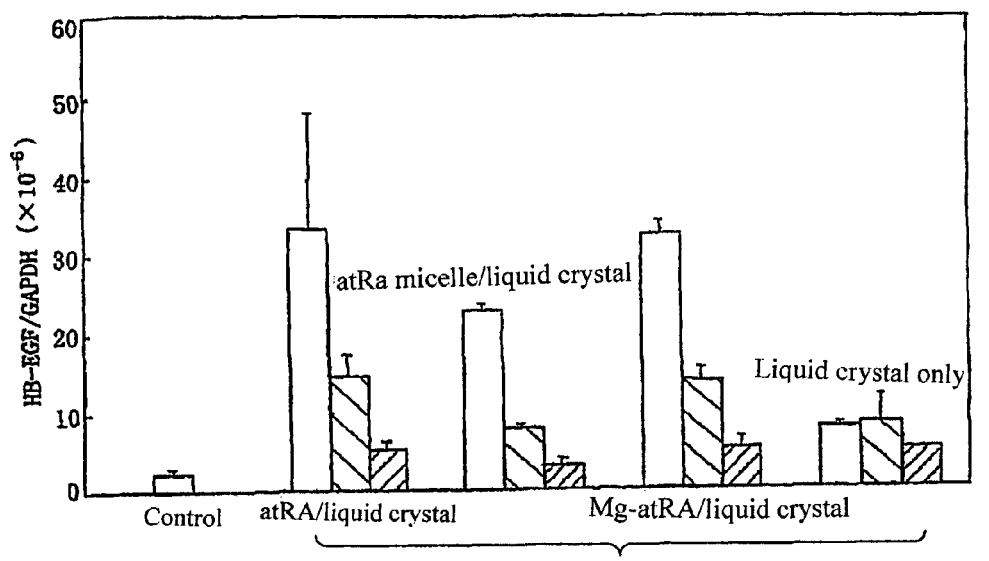
FIG. 3 is a graph which shows the changes in production amount of HB-EGF when each of the four kinds of samples is applied and production amount of HB-EGF of the skin to which nothing is applied in Example 3.

In accordance with the same manner as in Example 2, changes in the production amounts of HB-EGF by application of the following four kinds of samples were measured whereby each effects to transdermal absorption of retinoic acid was evaluated. The result is shown in FIG. 3 together with the production amount of HB-EGF of the skin to which nothing was applied. As will be apparent from FIG. 3, when retinoic acid was compounded with the lyotropic liquid crystal, transdermal absorption of retinoic acid was improved and production amount of HB-EGF increased independently of its compounding form. The lyotropic liquid crystal itself also showed an increasing action of HB-EGF production and the lyotropic liquid crystal was found to be able to be an effective ingredient of a dermal regeneration enhancer.

(a) Lyotropic liquid crystal compounded with fine particles of magnesium carbonate in which retinoic acid was included according to the formulation 1 of Example 1 (Mg-atRA/liquid crystal)

(b) Lyotropic liquid crystal compounded with the mixed micelle of retinoic acid and nonionic surfactant obtained in the preparation of fine particles of magnesium carbonate in which retinoic acid was included in the step 1 of Example 1 so as to make the compounding amount of retinoic acid same as that of the liquid crystal of the formulation 1 of Example 1 (atRA micelle/liquid crystal)

(c) Lyotropic liquid crystal compounded with retinoic acid itself so as to make the compounding amount of retinoic acid same as that of the liquid crystal of the formulation 1 of Example 1 (atRA/liquid crystal)

(d) Lyotropic liquid crystal prepared in the step 2 of Example 1 (liquid crystal only)

Example 4

Figure 4:
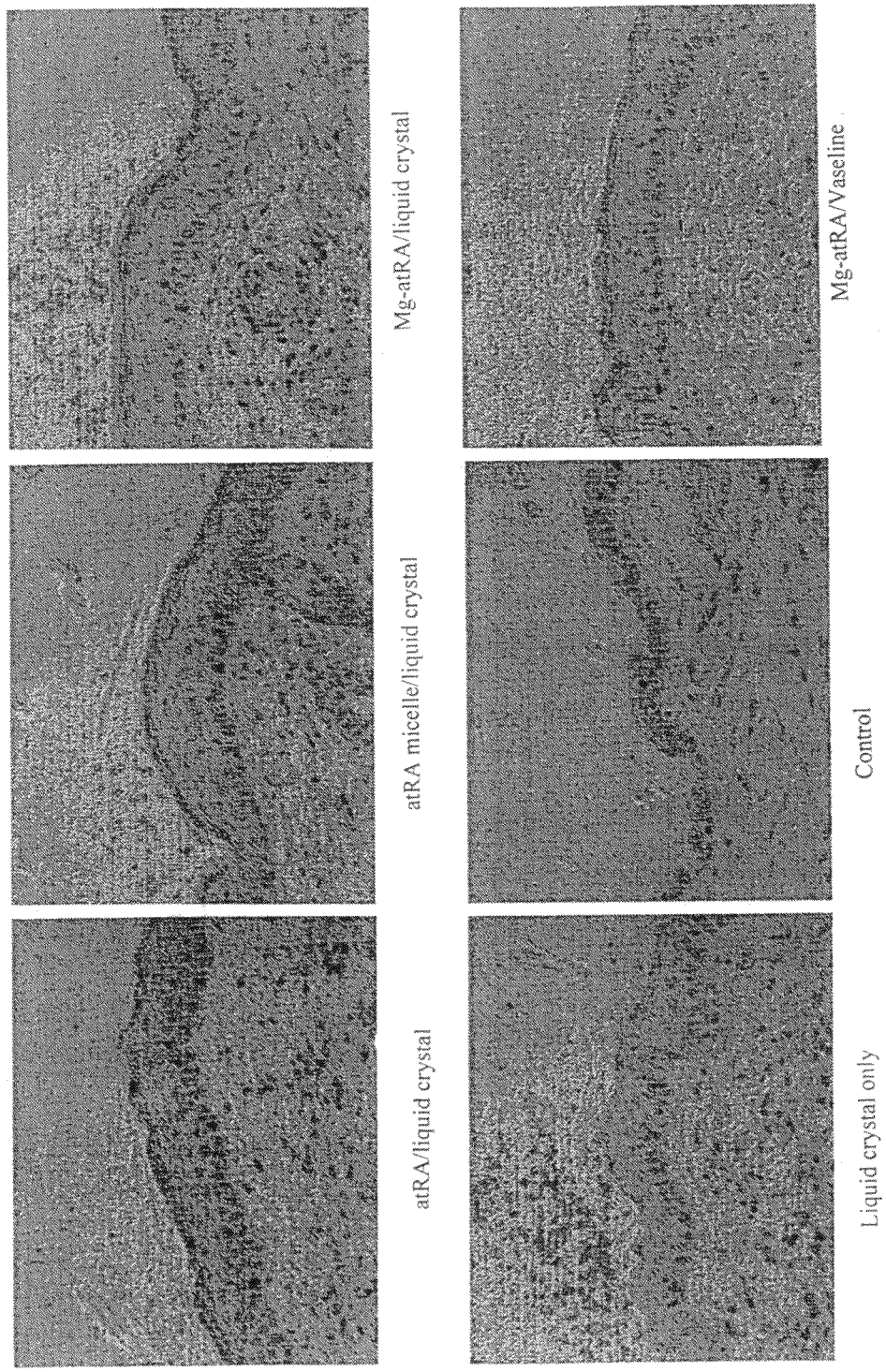
FIG. 4 is a cross-sectional picture of the skin when each of the five kinds of samples is applied and a cross-sectional picture of the skin to which nothing is applied in Example 5.

Back of colored guinea pigs having melanin pigment-producing cells (Weiser Maples; five weeks age; male) was shaved, the shaved part was washed with lukewarm water and each 30 mg of the following five kinds of samples was applied to an area of 2 cm×5 cm thereof. After 3 days from the application date under irradiation with any of UVA, UVB and UVA+UVB, skin of the part to which the sample was applied was collected and the slice was fixed with formalin, embedded in paraffin and stained by a Fontana-Masson method where melanin pigment was stained out in black to evaluate the dermal regeneration enhancing action. Cross-sectional pictures of the skin to which each of the samples was applied are shown in FIG. 4 together with the cross-sectional picture of the skin to which nothing was applied. As will be apparent from FIG. 4, thickening of the epidermis was noted in the case where the lyotropic liquid crystal compounded with retinoic acid in various forms was applied and in the case where the lyotropic liquid crystal itself was applied.

(a) Lyotropic liquid crystal compounded with fine particles of magnesium carbonate in which retinoic acid was included according to the formulation 1 of Example 1 (Mg-atRA/liquid crystal)

(b) Lyotropic liquid crystal compounded with the mixed micelle of retinoic acid and nonionic surfactant obtained in the preparation of fine particles of magnesium carbonate in which retinoic acid was included in the step 1 of Example 1 so as to make the compounding amount of retinoic acid same as that of the liquid crystal of the formulation 1 of Example 1 (atRA micelle/liquid crystal)

(c) Lyotropic liquid crystal compounded with retinoic acid itself so as to make the compounding amount of retinoic acid same as that of the liquid crystal of the formulation 1 of Example 1 (atRA/liquid crystal)

(d) Lyotropic liquid crystal prepared in the step 2 of Example 1 (liquid crystal only)

(e) Vaseline compounded with fine particles of magnesium carbonate in which retinoic acid was included so as to make the compounding amount of retinoic acid same as that of the liquid crystal of the formulation 1 of Example 1 (Mg-atRA/vaseline)

Example 5

Figure 5:
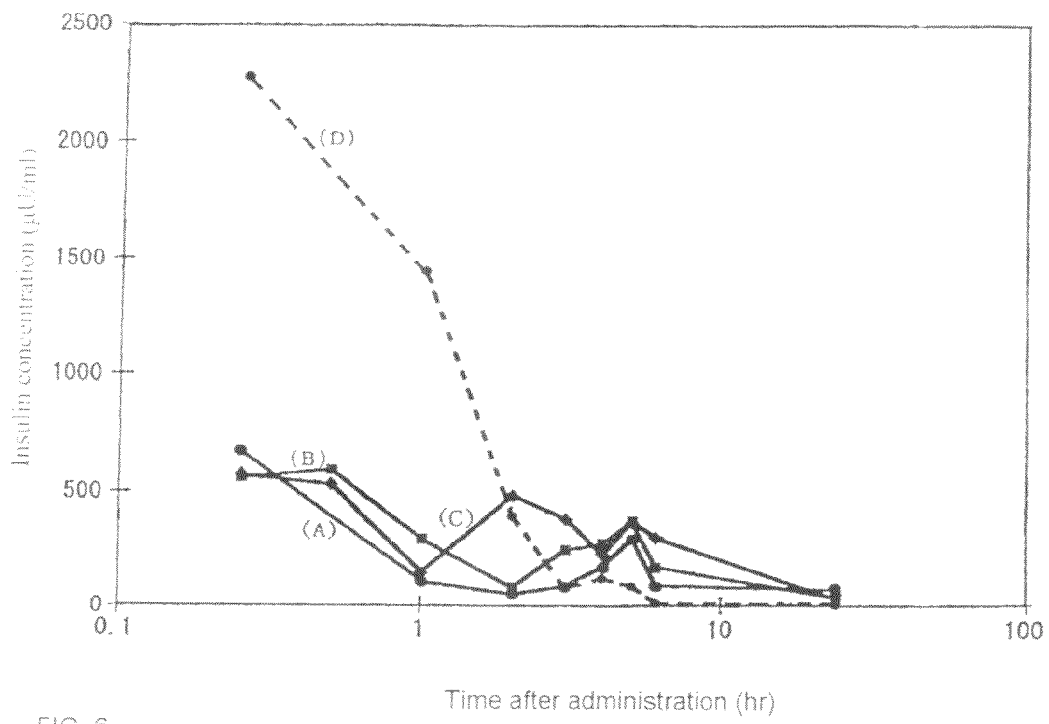
FIG. 5 is a graph which shows the changes in concentration of insulin in blood in Example 5.

Lyotropic liquid crystal compounded with 0.5%, 1% and 3% (by weight) of insulin (the lyotropic liquid crystal itself was a product prepared by the step 2 of Example 1) was prepared and concentration of insulin in blood was measured by the same manner as in Example 1. As a comparative example, 0.2 mg/200 µL of insulin was hypodermically injected and concentration of insulin in blood was measured. The result is shown in FIG. 5. Incidentally, (A) to (D) in FIG. 5 are as follows.

(A): The result when the lyotropic liquid crystal compounded with 0.5% (by weight) of insulin was applied (B): The result when the lyotropic liquid crystal compounded with 1% (by weight) of insulin was applied (C): The result when the lyotropic liquid crystal compounded with 3% (by weight) of insulin was applied (D): The result when 0.2 mg/200 µL of insulin was hypodermically injected As will be apparent from FIG. 5, although the initial concentration of insulin in blood when the lyotropic liquid crystal compounded with insulin was applied was less than the initial concentration of insulin in blood when insulin was hypodermically injected, the concentration of insulin in blood when insulin was hypodermically injected thereafter quickly decreased while, in case the lyotropic liquid crystal compounded with insulin was applied, the concentration of insulin in blood was maintained in a relatively high level. From the result as such, it was found that, when insulin was compounded with the lyotropic liquid crystal, insulin was now able to be transdermically absorbed in a sustained-release manner.

Example 6

Figure 6:
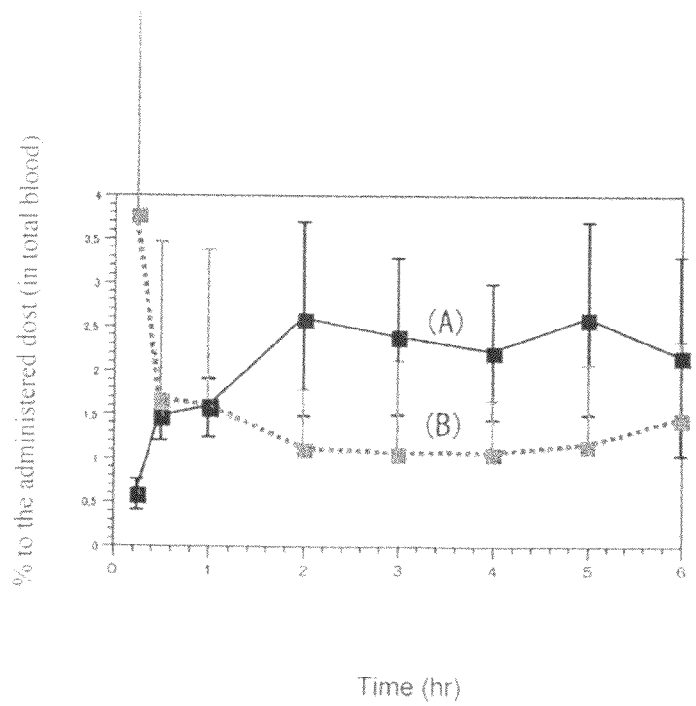
FIG. 6 is a graph which shows the changes in rate of niacinamide in total blood to the administered dose with the passage of time in Example 6.

Back of Wistar rats (seven weeks age; male) was shaved, the shaved part was washed with lukewarm water and each 30 mg of the two kinds of samples which were (A) a lyotropic liquid crystal compounded with 2% (by weight) of $^{14}C$ niacinamide (the lyotropic liquid crystal itself was a product prepared by the step 2 of Example 1) and (B) an aqueous gel (carboxyvinyl polymer; trade name: "Carbopol", Nikko Chemicals) compounded with 2% (by weight) of $^{14}C$ niacinamide was applied to an area of 2 cm×2 cm thereof. During the period of after 15 minutes to 6 hours from the application, blood was collected and radiation activity of $^{14}C$ contained in 200 µL of blood was measured whereby the rate (%) of niacinamide in total blood to the administered dose was calculated. The result is shown in FIG. 6. As will be apparent from FIG. 6, it was found that, when niacinamide was compounded with the lyotropic liquid crystal, niacinamide was apt to be included into blood and its concentration in blood was maintained in a relatively highly level for a long period. The above result is believed to be due to the fact that, although niacinamide is a substance which is usually very difficult to be absorbed transdermically since it is a water-soluble substance, it is permeated from the skin surface due to a enhancing action of the lyotropic liquid crystal for transdermal absorption whereby it is included into blood from capillary blood vessels in dermis.

Example 7

Figure 7:
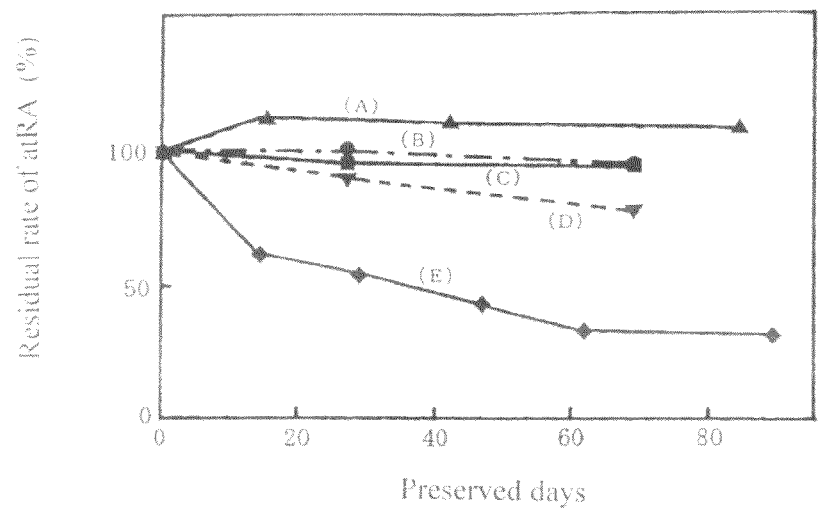
FIG. 7 is a graph which shows the changes in residual rate of retinoic acid in the five kinds of samples with the passage of time in Example 7.

Changes in the residual rate of retinoic acid with the passage of time when the following five kinds of samples were stored at 40° C. were checked. The result is shown in FIG. 7. As will be apparent from FIG. 7, when fine particles of inorganic acid salt with divalent metal in which retinoic acid was included were compounded with the lyotropic liquid crystal, it was found that retinoic acid remained stably even at the stage when 60 days elapsed from the preparation.

(A) Lyotropic liquid crystal compounded with fine particles of zinc carbonate in which retinoic acid was included so as to make the compounding amount of retinoic acid to the lyotropic liquid crystal 0.1% by weight (B) Lyotropic liquid crystal compounded with fine particles of calcium carbonate in which retinoic acid was included in the same manner (C) Lyotropic liquid crystal compounded with fine particles of calcium phosphate in which retinoic acid was included in the same manner (D) Lyotropic liquid crystal compounded with fine particles of magnesium carbonate in which retinoic acid was included in the same manner (E) Vaseline where retinoic acid itself was compounded therein so as to make the compounding amount of retinoic acid to the lyotropic liquid crystal 0.1% by weight Note: The sample (B) corresponds to the lyotropic liquid crystal compounded with fine particles of calcium carbonate in which retinoic acid was included according to the formulation 1 of Example 1 while the sample (D) corresponds to the lyotropic liquid crystal compounded with fine particles of magnesium carbonate in which retinoic acid was included according to the formulation 1 of Example 1. The samples (A) and (C) were prepared in accordance with the method for the preparation of the samples (B) and (D).

Example 8

Figure 8:
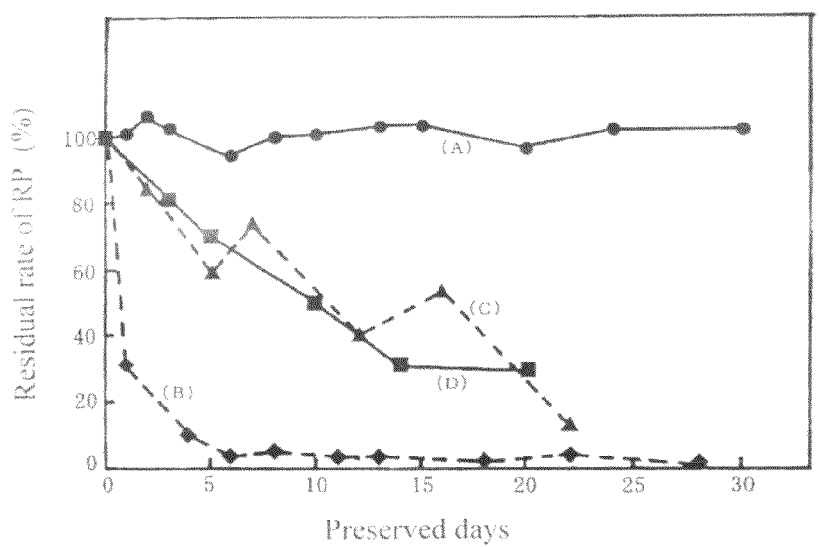
FIG. 8 is a graph which shows the changes in residual rate of retinol palmitate in the four kinds of samples with the passage of time in Example 8.

Changes in the residual rate of retinol palmitate with the passage of time when the following four kinds of samples were stored at 40° C. were checked. The result is shown in FIG. 8. As will be apparent from FIG. 8, when retinol palmitate was compounded with the lyotropic liquid crystal, it was found that retinol palmitate remained stably even at the stage when 30 days elapsed from the preparation.

(A) Lyotropic liquid crystal compounded with 0.1% (by weight) of retinol palmitate (the lyotropic liquid crystal itself was a product prepared by the step 2 of Example 1)

(B) 0.1% (w/w) ethanol solution of retinol palmitate (C) Ethanol solution where an antioxidant (BHT) was added to the ethanol solution (B)

(D) Nano-particles in which retinol palmitate was included, prepared in accordance with the method for the preparation of the nano-particles in which retinoic acid was included in the step 1 of Example 1 (containing 0.1% by weight of retinol palmitate)

Example 9

Figure 9:
FIG. 9 is a cross-sectional picture of the skin to which lyotropic liquid crystal compounded with SOD is applied in Example 9.
Figure 10:
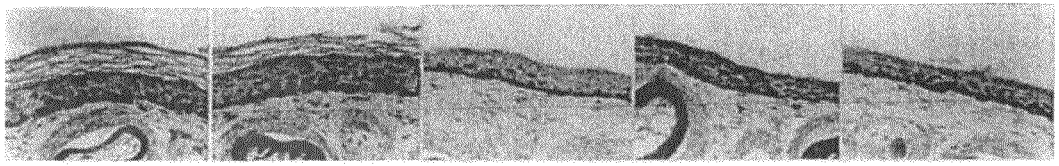
FIG. 10 is a cross-sectional picture of the skin to which a dispersion solution where SOD is dispersed in water is applied in the same.
Figure 11:
FIG. 11 is a cross-sectional picture of the skin to which only water is applied in the same.

Back of colored guinea pigs having melanin pigment-producing cells (Weiser Maples; five weeks age; male) was shaved, the shaved part was washed with lukewarm water, 30 mg of the lyotropic liquid crystal compounded with 0.1% (by weight) of SOD having a suppressive action to melanin pigment production (molecular weight: 32,000) was applied to an area of 1.5 cm×1.5 cm thereof and the influence on the epidermis was checked by the method mentioned in Example 4. A cross-sectional picture of the skin (stained by a Fontana-Masson method) is shown in FIG. 9. Further, a cross-sectional picture of the skin (stained by a Fontana-Masson method) when 30 μL of a dispersion solution where 0.1% (by weight) of SOD was dispersed in water was applied is shown in FIG. 10 and a cross-sectional picture of the skin (stained by a Fontana-Masson method) when 30 μL of water only was applied is shown in FIG. 11. As will be apparent from FIG. 9 to FIG. 11, when the lyotropic liquid crystal compounded with SOD was applied, amount of melanin pigment in the epidermis significantly decreased (being judged from the fact that black spots and areas were little) as compared with the case where a dispersion solution where SOD was dispersed in water was applied or the case where only water was applied. That was believed to be due to the fact that SOD penetrated through horny layer and reached into the epidermis. Incidentally, thickening of the epidermis noted upon application of the lyotropic liquid crystal compounded with SOD was believed to be due to the dermal regeneration enhancing action of the lyotropic liquid crystal itself.

Example 10

Figure 12:
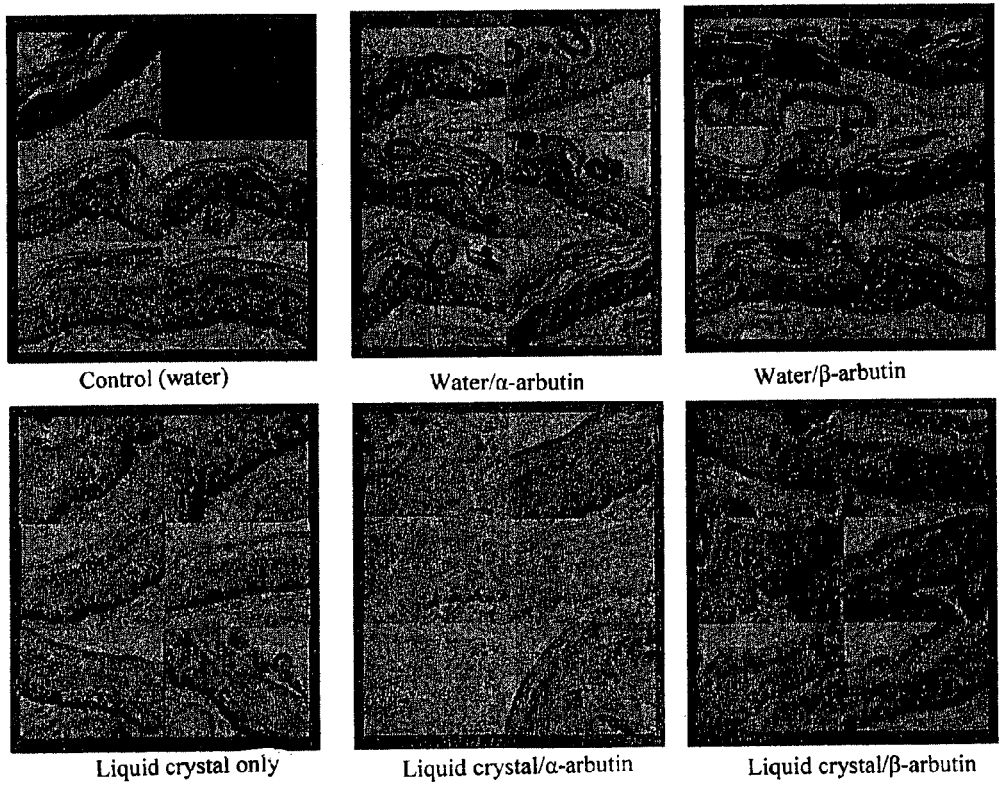
FIG. 12 is a cross-sectional picture of the skin to which each of the six kinds of samples is applied in Example 10.

According to the same manner as in Example 9, the influence of the following six kinds of samples on the epidermis was checked. Cross-sectional pictures of the skin (stained by a Fontana-Masson method) are shown in FIG. 12. As will be apparent from FIG. 12, amount of melanin pigment in the epidermis significantly decreased when arbutin having a suppressive action to melanin pigment production was compounded with the lyotropic liquid crystal and applied. Since thickening of the epidermis was also noted even when the lyotropic liquid crystal only was applied, it was confirmed that the lyotropic liquid crystal itself had a dermal regeneration enhancing action.

(a) Lyotropic liquid crystal compounded with 2% (by weight) of α-arbutin (molecular weight: 272; Ezaki Glico Co., Ltd.)

(b) Lyotropic liquid crystal compounded with 2% (by weight) of β-arbutin (molecular weight: 272; Hayashibara Co., Ltd.)

(c) Lyotropic liquid crystal only (d) Dispersion solution where 2% (by weight) of α-arbutin was dispersed in water (e) Dispersion solution where 2% (by weight) of β-arbutin was dispersed in water (f) Water only Example 11

Figure 13:
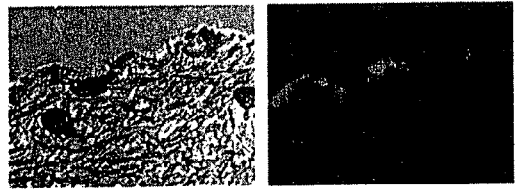
FIG. 13 is a fluorescent cross-sectional picture of the skin to which lyotropic liquid crystal compounded with oligo-DNA fluorescently labeled with FITC is applied in Example 11.
Figure 14:
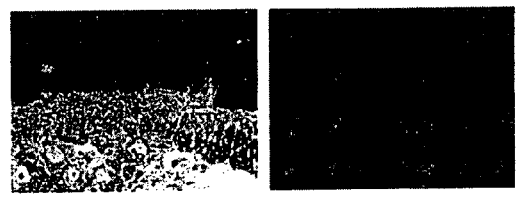
FIG. 14 is a fluorescent cross-sectional picture of the skin to which a dispersion solution where oligo-DNA fluorescently labeled with FITC is dispersed in water is applied in the same.

Back of ddY mice (seven weeks age; male) was shaved, the shaved part was washed with lukewarm water and 30 mg of the lyotropic liquid crystal compounded with 2% (by weight) of oligo-DNA (molecular weight: 8899) fluorescently labeled with fluorescein isothiocyanate (FITC) was applied to an area of 1.5 cm×1.5 cm thereof. After two hours from the application, skin of the part to which the sample was applied was collected, made into a frozen slice and subjected to a fluorescent observation. A fluorescent cross-sectional picture of the skin is shown in FIG. 13. Another fluorescent cross-sectional picture of the skin to which 30 μL of a dispersion solution where 2% (by weight) of oligo-DNA fluorescently labeled with FITC was dispersed in water was applied is shown in FIG. 14. As will be apparent from FIG. 13 and FIG. 14, the oligo-DNA was permeated into the epidermis after two hours from the application when it was compounded with the lyotropic liquid crystal and applied.

Example 12

Figure 15:
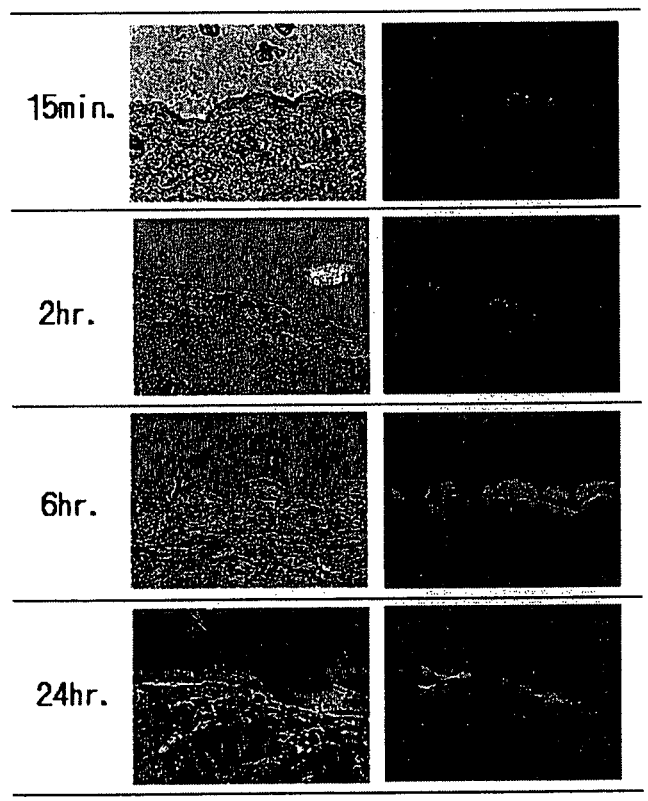
FIG. 15 is a fluorescent cross-sectional picture of the skin to which lyotropic liquid crystal compounded with fluorescently labeled dextran (molecular weight: 4,000) with FITC is applied in Example 12.

According to the same manner as in Example 11, penetratability into the skin was checked when the lyotropic liquid crystal compounded with 5% (by weight) of dextran (molecular weight: 4,000) fluorescently labeled with FITC was applied. A fluorescent cross-sectional picture of the skin is shown in FIG. 15. As will be apparent from FIG. 15, dextran was permeated into the epidermis within 15 minutes and, with the passage of time, it was further permeated thereinto when it was compounded with the lyotropic liquid crystal and applied.

Example 13

Figure 16:
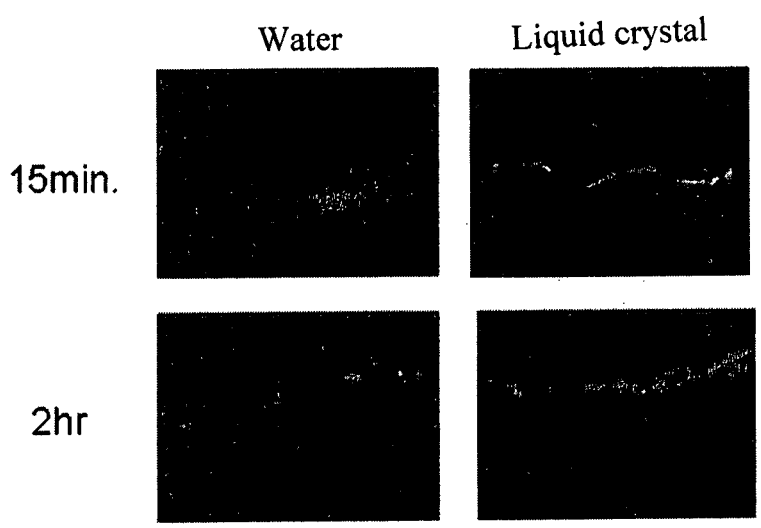
FIG. 16 is a fluorescent cross-sectional picture of the skin to which lyotropic liquid crystal compounded with fluorescently labeled dextran (molecular weight: 70,000) with FITC is applied and a fluorescent cross-sectional picture of the skin to which a dispersion solution where fluorescently labeled dextran (the same as above) is dispersed in water is applied in Example 13.

According to the same manner as in Example 11, penetratability into the skin was checked when the lyotropic liquid crystal compounded with 5% (by weight) of dextran (molecular weight: 70,000) fluorescently labeled with FITC was applied. Also, penetratability into the skin was checked when 30 μL of a dispersion solution where 5% (by weight) of dextran (the same one as above) fluorescently labeled with FITC was dispersed in water was applied. Fluorescent cross-sectional picture of the skin for each of the above cases is shown in FIG. 16. As will be apparent from FIG. 16, dextran was permeated into the epidermis within 15 minutes and, with the passage of time, it was further permeated thereinto when it was compounded with the lyotropic liquid crystal and applied.

Example 14

A lyotropic liquid crystal comprising 16.819% by weight of squalane, 8.931% by weight of soybean lecithin, 4.466% by weight of cholesterol, 15.026% by weight of POE (60) hydrogenated castor oil, 38.897% by weight of glycerol and 15.860% by weight of distilled water was prepared. When the lyotropic liquid crystal was previously applied on the skin surface and then retinoic acid was added thereto later, transdermal absorption of retinoic acid was able to be improved.

Preparation Example 1

A commercially available antiseptic was added to the lyotropic liquid crystal of Example 14 to prepare a product.

Preparation Example 2

The lyotropic liquid crystal of Example 14 was compounded with a home-made lotion base (milky liquid) and then a commercially available antiseptic was added thereto to prepare a lotion. The lotion base was prepared by mixing of soybean lecithin, cholesterol, PEG 4000, cyclic silicone, Carbopol (macromolecular gelling agent), Keltrol (macromolecular gelling agent) and distilled water followed by emulsifying.

INDUSTRIAL APPLICABILITY

The present invention has an industrial applicability in such a respect that there is provided a transdermal absorption enhancer as a novel pharmaceutical use of lyotropic liquid crystal which has been utilized as a basic material for pharmaceutical preparations for external application and for cosmetics.

The invention claimed is:

1. A method of transdermally administering an active ingredient, comprising:
    applying a lyotropic liquid crystal compounded with the active ingredient to a skin surface of a person in need of transdermal administration of the active ingredient,
    wherein said lyotropic liquid crystal contains 15.026% by weight to 28% by weight of a surfactant and 5% by weight to 80% by weight of water,
    wherein said active ingredient is a macromolecular substance having a molecular weight of not less than 1,000 daltons,
    wherein said surfactant is polyoxyethylene octyl dodecyl ether,
    wherein said lyotropic liquid crystal further contains 16.819% by weight to 25% by weight of squalane,
    wherein said lyotropic liquid crystal further contains 1% by weight to 55% by weight of glycerol.

2. The method of claim 1, wherein said lyotropic liquid crystal further contains 0.01% by weight to 10% by weight of an auxiliary surfactant.

3. The method of claim 2, wherein said auxiliary surfactant is cholesterol.

4. The method of claim 1, wherein said active ingredient is at least one member selected from the group consisting of organic compound, peptide, protein, oligonucleotide, DNA and RNA.

5. The method of claim 1, wherein said macromolecular substance is a water-soluble substance.

6. The method of claim 1, wherein said active ingredient is included in the inside of fine particles of inorganic acid salt with divalent metal.

7. The method of claim 1, wherein said active ingredient is compounded in an amount of 0.01% by weight to 50% by weight to the lyotropic liquid crystal.

8. The method of claim 1, wherein the ratio of each component in the lyotropic liquid crystal is as follows:
    polyoxyethylene octyl dodecyl ether: 28% by weight,
    squalane: 25% by weight,
    water: 16% by weight, and
    glycerol: 31% by weight.

9. The method of claim 1, wherein the ratio of each component in the lyotropic liquid crystal is as follows:
    polyoxyethylene octyl dodecyl ether: 15.026% by weight,
    squalane: 16.819% by weight,
    water: 15.860% by weight, and
    glycerol: 38.897% by weight.

10. The method of claim 1, wherein said lyotropic liquid crystal contains 10% by weight to 60% by weight of water.

11. The method of claim 1, wherein said lyotropic liquid crystal contains 13% by weight to 50% by weight of water.

* * * * *